United States Patent [19]

Rao et al.

[11] 4,018,827

[45] Apr. 19, 1977

[54] PROCESS FOR THE PREPARATION OF CYCLOALKANE-1,2-DIONES

[75] Inventors: Durvasula V. Rao, Cheshire; Fred A. Stuber, North Haven, both of Conn.

[73] Assignee: The Upjohn Company, Kalamazoo, Mich.

[22] Filed: Feb. 25, 1976

[21] Appl. No.: 661,285

[52] U.S. Cl. .................... 260/586 P; 260/586 M; 260/537 R
[51] Int. Cl.[2] .......................................... C07C 45/00
[58] Field of Search ........ 260/586 P, 586 M, 537 R

[56] References Cited

UNITED STATES PATENTS

| 2,662,921 | 12/1953 | Middleton | 260/586 P |
| 3,153,066 | 10/1964 | Werber | 260/586 P |
| 3,679,753 | 7/1972 | Greco | 260/586 P |

Primary Examiner—Norman Morgenstern
Attorney, Agent, or Firm—Denis A. Firth; John Kekich

[57] ABSTRACT

Cycloalkanones ($C_{5-12}$) are converted to the corresponding 1,2-cycloalkanediones by autoxidation in the presence of a base catalyst (potassium t-butoxide preferred) and a polar organic solvent.

12 Claims, No Drawings

PROCESS FOR THE PREPARATION OF CYCLOALKANE-1,2-DIONES

BACKGROUND OF THE INVENTION

1. Field of the Invention

This invention relates to the preparation of 1,2-cycloalkanediones and is more particularly concerned with the preparation of 1,2-cycloalkanediones by autoxidation of the corresponding cycloalkanones.

2. Description of the Prior Art

A number of methods for the preparation of 1,2-cycloalkanediones are known. Illustratively, 1,2-cyclohexanedione has been obtained by brominating cyclohexanone and hydrolyzing the 2,6-dibromocyclohexanone to the corresponding dihydroxycyclohexanone which then loses water to yield the dione; see Wallach et al., Annalen 437, 172, 1924. 1,2-cyclohexanedione has also been obtained by heating divinyl glycol with copper (Urion, Comptes rendus 192, 1662, 1931) and by oxidizing cyclohexanone with selenium dioxide in ethanolic solution (Riley et al., J. Chem. Soc. 1932, 1875). A procedure involving the oxidation of cyclohexanone with selenious acid or selenium dioxide in aqueous dioxan is described in Organic Synthesis, Collective Volume IV, 1963, 229, John Wiley and Sons Inc., New York.

We have now found that 1,2-cyclohexanedione and like 1,2-cycloaliphatic diketones can be prepared readily and in good yield by autoxidation of the corresponding cycloalkanones using readily available and inexpensive reagents.

SUMMARY OF THE INVENTION

The invention comprises a process for the autoxidation of a cycloalkanone to the corresponding 1,2-cycloalkanedione which process comprises reacting said alkanone with oxygen in the presence of a base and a polar organic solvent at a temperature not exceeding about −20° C.

The 1,2-cycloalkanediones obtained in accordance with the process of the invention are well known in the art and are useful as chemical intermediates in a variety of ways. For example, 1,2-cyclohexanedione can be dehydrogenated using known procedures (for example, heating in the presence of a palladium on charcoal catalyst) to yield catechol which is a dihydric phenol well-known to be useful as an antioxidant, photographic chemical and the like. The 1,2-cycloalkanediones are also known to yield dithiosemicarbazides which, in the form of metal chelates, are useful in the treatment of coccidiosis; see U.S. Pat. No. 3,382,266. The 1,2-cycloalkanediones are also useful, in combination with carbodiimides, in the stabilization of polyurethanes against hydrolytic attack in accordance with U.S. Pat. No. 3,193,525.

DETAILED DESCRIPTION OF THE INVENTION

In carrying out the process of the invention the reactants are brought together at a temperature of the order of about −20° C or less. The reaction temperature can be as low as about −40° C but preferably is from about −20° to about −30° C. While the order in which the reactants are brought together is not critical, it is preferred that the cycloalkanone be added to the preformed mixture of base and polar solvent in the presence of oxygen. Thus, it is desirable that there always be an excess of base present in the reaction mixture. Further, it is also desirable that the cycloalkanone be not maintained in contact with the base in the absence of oxygen for a longer period than is absolutely necessary before the desired reaction commences, because of the tendency of the cycloalkanone to undergo self-condensation in the presence of said base.

The reaction is conducted in any appropriate closed vessel in which an oxygen atmosphere can be maintained. Advantageously oxygen is bubbled into the mixture of base and organic polar solvent prior to, and throughout, the addition of the cycloalkanone to the mixture. The base is advantageously employed in an amount corresponding to about 1.0 moles to about 2.0 moles per mole of cycloalkanone and preferably in an amount corresponding to about 1.1 moles to about 1.2 moles per mole of cycloalkanone. The amount of solvent employed is not critical and can vary over a wide range depending upon the relative solubility of the base in said solvent. The amount of solvent employed is generally dictated by economic considerations particularly where the process of the invention is to be carried out on a commercial scale.

The autoxidation generally proceeds rapidly and its progress can be followed by routine analytical procedures, such as infrared spectroscopy, nuclear magnetic resonance spectroscopy, and the like, carried out on aliquots of the reaction mixture. When the reaction has been carried to completion, the desired cycloalkanedione is isolated from the reaction mixture by routine procedures. Illustratively, the reaction mixture is acidified and the diketone which separates is extracted with solvent and then separated therefrom by evaporating the solvent.

In a preferred method of isolating the desired diketone from the reaction mixture, the latter is saturated with carbon dioxide to neutralize. The resulting mixture is diluted with organic solvent, filtered to remove insoluble material and the filtrate evaporated to isolate the diketone along with the unconverted starting ketone. The diketone is purified, if desired, by conventional procedures such as fractional distillation.

A by-product of the process of the invention is the saturated aliphatic dicarboxylic acid derived by cleavage of the diketone or products intermediate thereto. Illustratively, when the starting cycloalkanone is cyclohexanone, the dicarboxylic acid isolated as by-product is adipic acid and, in the case of cyclopentanone as starting material, the by-product is glutaric acid.

Such by-products are themselves valuable and can readily be isolated by conventional procedures; for example, the solvent extract containing the diketone, which is obtained after acidifying the reaction product and extracting with solvent, is washed with weak aqueous alkali such as sodium bicarbonate solution. The dicarboxylic acid passes into the aqueous layer and can be recovered therefrom by acidification. When cabon dioxide neutralization is employed, the dicarboxylic acid can be precipitated, for example, as the insoluble alkali metal salt.

The bases which are employed in the process of the invention are inclusive of alkali metal hydroxides such as sodium, potassium and lithium hydroxides and alkali metal alkoxides such as sodium, potassium and lithium methoxides, ethoxides, butoxides, pentoxides, hexoxides and the like. The preferred bases are the alkali metal alkoxides derived from alkanols having from 1 to 6 carbon atoms. The most preferred base is potassium tert.-butoxide.

The organic solvents employed in the process of the invention are advantageously ethers such as diethyl ether, dimethyl ether, dimethoxyethane, tetrahydrofuran, and the like which remain liquid at the reaction temperatures employed. In a preferred embodiment the solvent is a mixture of an ether, such as those exemplified above, and a minor amount (i.e. less than 50 percent by volume) of a polar organic solvent such as t-butyl alcohol, t-amyl alcohol, dimethylformamide, dimethylacetamide, dimethylsulfoxide, tetramethylene sulfone, hexamethylphosphoramide, tetramethylurea, and the like.

A particularly preferred combination of solvents for use in the process of the invention is a mixture of dimethoxyethane and tert.-butyl alcohol, the latter being present in the mixture in amount corresponding to about 20 to about 50 percent by volume of the mixture.

The cycloalkanones, which can be converted to the corresponding cycloalkanediones in accordance with the process of the invention, can be any cycloalkanone containing from 5 to 12 ring carbon atoms. One or more inert substituents can be present in the ring of the cycloalkanone provided that both carbon atoms in the α-position to the keto group in the ring are unsubstituted. By "inert substituent" is meant a substituent which is inert under the conditions of the reaction, i.e. does not itself enter into the reaction or otherwise interfere in any way with the desired course of the reaction. Illustrative of inert substituents are lower-alkyl, i.e. alkyl from 1 to 6 carbon atoms such as methyl, ethyl, propyl, butyl, pentyl, hexyl, and isomeric forms thereof; and lower-alkoxy, i.e. alkoxy from 1 to 6 carbon atoms such as methoxy, ethoxy, propoxy, butoxy, pentoxy, hexyloxy and isomeric forms thereof.

The process of the invention provides a means of converting cycloalkanone to the corresponding cycloalkanediones using relatively inexpensive and readily available reactants. In particular, the process of the invention avoids the use of relatively expensive oxidizing agents such as selenium dioxide and selenious acid which have been used hitherto. The process is readily adaptable to the commercial scale, gives good yields of the desired product, and provides, as the major by-product, a dicarboxylic acid which itself is in commercial demand.

The following examples describe the manner and process of making and using the invention and set forth the best mode contemplated by the inventors of carrying out the invention but are not to be construed as limiting.

EXAMPLE 1

A solution of 13 g (0.116 mole) of potassium t-butoxide in a mixture of 60 ml. of dimethoxyethane and 40 ml. of t-butyl alcohol was stirred in a three necked flask fitted with gas inlet tube, condenser and drying tube, and cooled to −30° C in a dry ice-acetone bath. A steady stream of oxygen (at a rate of 675 ml./min.) was bubbled through the reaction mixture. A total of 9.8 g. (0.1 mole) of cyclohexanone was added, with stirring, in a single portion. The temperature was maintained at about −20° C and stirring and bubbling of oxygen into the reaction mixture was continued for a period of 1 hour after the addition of cyclohexanone was complete. At the end of this time the reaction mixture was diluted with 100 ml. of water and extracted with 200 ml. of ethyl acetate. The aqueous layer was acidified by the addition of dilute hydrochloric acid and then extracted with 500 ml. of ethyl acetate. The ethyl acetate was washed with 5% aqueous sodium bicarbonate solution and then dried over anhydrous magnesium sulfate and evaporated to dryness. The residue was 4.0 g. (43.7% yield based on cyclohexanone converted) of cyclohexanedione-1,2. A total of 1.8 g. of cyclohexanone was recovered from the initial ethyl acetate extract of the reaction mixture and a total of 1.3 g. (10.9% yield based on cyclohexanone) of adipic acid was isolated by acidification of the sodium bicarbonate washings.

EXAMPLE 2

The procedure described in Example 1 was repeated exactly as set forth using identical reactants and reactant proportions, the only variation occurring in the method of working up the reaction mixture. At the end of the period of stirring at −20° C following addition of the cyclohexanone, the reaction mixture was acidified by the addition of 100 ml. of water containing 10 ml. of concentrated hydrochloric acid. The acidified mixture was immediately extracted with ethyl acetate, the latter extract was washed with 5% aqueous sodium bicarbonate and then evaporated to dryness. The resulting ethyl acetate solution was found by gas liquid phase chromatography to contain 5.6 g. (55.6% yield based on cyclohexanone converted) of cyclohexanedione-1,2 and 1 g. of cyclohexanone. The sodium bicarbonate washings were acidified to obtain 2 g. (15.2% yield based on cyclohexanone converted) of adipic acid.

EXAMPLE 3

The procedure described in Example 1 was repeated exactly as set forth using identical reactants and reactant proportions save that the rate at which oxygen was passed into the reaction mixture was increased to 1400 ml./min. and the method of working up the reaction mixture was changed as follows. At the end of the period of stirring at −20° C following addition of the cyclohexanone, the reaction mixture was purged with cabon dioxide until the pH of the reaction mixture was approximately 8. At this point the reaction mixture was diluted with ethyl acetate and then filtered to remove insoluble material (11.3 g.). The filtrate was found by gas liquid phase chromatography to contain 1.6 g. of cyclohexanone and 7.7 g. of cyclohexanedione-1,2 (representing a yield of 82% based on cyclohexanone converted). The insoluble material recovered in the filtrate was dissolved in water and the solution acidified to obtain 1.3 g. (10.6% yield) of adipic acid.

EXAMPLE 4

A solution of 10.8 g. (0.2 mole) of sodium methoxide in a mixture of 30 ml. of hexamethylphosphoramide and 100 ml. of dimethoxyethane was stirred in a three-necked flask fitted with gas inlet tube, condenser and drying tube, and cooled to −20° C. The temperature was maintained there throughout the whole of the subsequent operations. A stream of oxygen was bubbled in at a rate of 1400 ml./min. and thereafter 9.8 g. (0.1 mole) of cyclohexanone was added slowly over a period of 0.5 hour. The resulting mixture was stirred at −20° C with constant bubbling of oxygen for a period of 1 hour after the addition was complete. At the end of this period the product was isolated using the procedure described in Example 1. There was thus obtained 4 g. (41.6% yield) of cyclohexanedione-1,2, 1.4 g.

(14.3%) of recovered cyclohexanone and 3.1 g. (24.7% yield) of adipic acid.

EXAMPLE 5

The procedure described in Example 4 was repeated with the sole exceptions that (1) the stream of oxygen was passed through a trap cooled in dry ice before entering the reaction vessel and (2) the reaction temperature was lowered to −40° C. The yield of cyclohexanedione-1,2 was 4.5 g. (47.4% based on cyclohexanone starting material) and the weight of recovered cyclohexanone was 1.5 g. (15.4%).

EXAMPLE 6

Using the procedure described in Example 1, but replacing the potassium t-butoxide there used by 12.1 g. (0.11 mol.) of sodium t-amyloxide and the t-butyl alcohol by t-amyl alcohol, there was obtained 2.0 g. (46% yield based on cyclohexanone reacted) of cyclohexanedione-1,2, 6.0 g. (62% yield) of recovered cyclohexanone and 1.2 g. (21.2% based on cyclohexanone reacted) of adipic acid.

EXAMPLE 7

A mixture of 9.8 g. (0.1 mole) of cyclohexanone and 30 ml. of hexamethylphosphoramide was stirred and cooled at −20° C while oxygen was bubbled through the mixture for 10 minutes at a rate of 1400 ml.min. A total of 11.2 g. (0.2 mole) of powdered potassium hydroxide pellets was added to the mixture and the latter was stirred at −20° to −15° C with continuous oxygen bubbling for a total of 2 hours. The resulting mixture was diluted with water and extracted with ethyl acetate from which was isolated 8.5 g. of unchanged cyclohexanone. The aqueous layer was acidified with hydrochloric acid and extracted with ethyl acetate. From the organic layer, by aqueous sodium bicarbonate extraction, was isolated 0.4 g. of adipic acid. The organic layer after drying over anhydrous magnesium sulfate was evaporated to dryness to yield 0.6 g. (40.3% based on cyclohexanone converted) of cyclohexanedione-1,2.

We claim:
1. A process for the autoxidation of a cycloalkanone to the corresponding cycloalkane-1,2-dione which process comprises reacting said cycloalkanone with oxygen in the presence of (i) from 1 to 2 mole, per mole of cycloalkanone, of a base selected from the class consisting of alkali metal hydroxides and alkali metal alkoxides and (ii) an organic polar solvent at a temperature not exceeding about −20° C.
2. The process of claim 1 wherein said base is an alkali metal hydroxide.
3. The process of claim 1 wherein said base is an alkali metal alkoxide.
4. The process of claim 3 wherein said alkali metal alkoxide is potassium tertiary-butoxide.
5. The process of claim 1 wherein said organic solvent is dimethoxyethane.
6. The process of claim 1 wherein said organic solvent comprises a mixture of dimethoxyethane and t-butyl alcohol.
7. The process of claim 1 wherein the cycloalkanone is cyclohexanone whereby there is produced 1,2-cyclohexanedione.
8. A process for the conversion of cyclohexanone to 1,2-cyclohexanedione which comprises reacting cyclohexanone with oxygen in the presence of (i) from 1 to 2 mole, per mole of cyclohexanone, of a base selected from the class consisting of alkali metal hydroxides and alkali metal alkoxides and (ii) an organic polar solvent at a temperature not exceeding about −20° C.
9. The process of claim 8 wherein said base is an alkali metal alkoxide.
10. The process of claim 9 wherein the alkali metal alkoxide is a potassium tert.-butoxide.
11. The process of claim 8 wherein the organic solvent is dimethoxyethane.
12. The process of claim 8 wherein the organic solvent comprises a mixture of dimethoxyethane and t-butyl alcohol.

* * * * *